(12) United States Patent
Steiner

(10) Patent No.: US 10,342,927 B2
(45) Date of Patent: Jul. 9, 2019

(54) OPERATION MEMBER AND MECHANISM FOR A DRUG DELIVERY DEVICE, AND DRUG DELIVERY DEVICE

(71) Applicant: Sanofi-Aventis Deutschland GmbH, Frankfurt am Main (DE)

(72) Inventor: Patrick Steiner, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 374 days.

(21) Appl. No.: 15/100,380

(22) PCT Filed: Dec. 8, 2014

(86) PCT No.: PCT/EP2014/076810
§ 371 (c)(1),
(2) Date: May 31, 2016

(87) PCT Pub. No.: WO2015/086481
PCT Pub. Date: Jun. 18, 2015

(65) Prior Publication Data
US 2016/0303325 A1    Oct. 20, 2016

(30) Foreign Application Priority Data
Dec. 9, 2013  (EP) .................................... 13196224

(51) Int. Cl.
*A61M 5/315*  (2006.01)
*A61M 5/24*  (2006.01)

(52) U.S. Cl.
CPC ............ *A61M 5/3155* (2013.01); *A61M 5/24* (2013.01); *A61M 5/31535* (2013.01); *A61M 5/31551* (2013.01); *A61M 2005/2485* (2013.01)

(58) Field of Classification Search
CPC ............ A61M 5/3155; A61M 5/31535; A61M 5/31551; A61M 5/24
See application file for complete search history.

(56) References Cited

U.S. PATENT DOCUMENTS 4,003,622 A    1/1977  Gartland
2011/0098658 A1*  4/2011  Enggaard ............ A61M 5/3155
604/207
(Continued)

FOREIGN PATENT DOCUMENTS

CN    102245233    9/2014
CN    102939123    11/2014
(Continued)

OTHER PUBLICATIONS

International Search Report and Written Opinion in International Application No. PCT/EP2014/076810, dated Feb. 12, 2015, 10 pages.
(Continued)

*Primary Examiner* — Laura A Bouchelle
(74) *Attorney, Agent, or Firm* — Fish & Richardson P.C.

(57) ABSTRACT

The operation member (11) has a central opening (17) with a periphery (18) and at least one protruding element (20) arranged on the periphery and extending into the opening, which is surrounded by a protruding rim (21). The protruding rim is interrupted along the periphery by at least one gap (22). If more than one gap is provided, the gaps are arranged such that the pattern of the gaps does not comprise a symmetry that would allow a rotation different from an integer multiple of 360° around a central axis of the opening to map the complete pattern of gaps onto itself. The operation member may be combined with a drive member comprising abutments in positions corresponding to the positions of the gaps.

17 Claims, 2 Drawing Sheets

(56) References Cited

U.S. PATENT DOCUMENTS

2011/0319835 A1   12/2011   Burren
2012/0041389 A1    2/2012   Giambattista et al.
2013/0035644 A1    2/2013   Giambattista et al.

FOREIGN PATENT DOCUMENTS

| WO | WO 2004/078239 | 9/2004 |
| WO | WO 2006/045526 | 5/2006 |
| WO | WO 2008/016381 | 2/2008 |
| WO | WO 2009/098299 | 8/2009 |
| WO | WO 2011/131777 | 10/2011 |
| WO | WO 2012/045793 | 12/2012 |
| WO | WO 2013/156345 | 10/2013 |
| WO | WO 2014/056874 | 4/2014 |

OTHER PUBLICATIONS

International Preliminary Report on Patentability in International Application No. PCT/EP2014/076810, dated Jun. 14, 2016, 7 pages.
Rote Liste, "50. Hypophysen-, Hypothalamushormone, andere regulatorische Peptide u. ihre Hemmstoffe," Chapter 50, ed. 2008, 20 pages.

* cited by examiner

OPERATION MEMBER AND MECHANISM FOR A DRUG DELIVERY DEVICE, AND DRUG DELIVERY DEVICE

CROSS-REFERENCE TO RELATED APPLICATIONS

This application is a U.S. national stage application under 35 USC § 371 of International Application No. PCT/EP2014/076810, filed on Dec. 8, 2014, which claims priority to European Patent Application No. 13196224.3, filed on Dec. 9, 2013, the entire contents of which are incorporated herein by reference.

The present invention relates to the operation member of a mechanism for a drug delivery device and to a drug delivery device incorporating such a mechanism.

WO 2004/078239 A1 discloses a drive mechanism for drug delivery devices, which comprises a dose dial grip, a dose dial sleeve and a drive sleeve, which serves to advance a piston rod for drug delivery. The dose dial grip is secured to the dose dial sleeve to prevent a relative movement between these components. During dose dialling the drive sleeve is temporarily rotationally coupled to the dose dial sleeve, so that the dose dial grip, the dose dial sleeve and the drive sleeve are simultaneously rotated. During drug dispensing the dose dial sleeve is no longer rotationally coupled to the drive sleeve. A relative axial movement between the dose dial grip and the drive sleeve is prevented by an engagement of protruding parts of the dose dial grip with an annular recess on the periphery of the drive sleeve, so that a relative rotation between the drive sleeve and the dose dial grip is allowed. The engagement between the protruding parts of the dose dial grip and the annular recess of the drive sleeve is to be maintained during operation.

Some aspects of the subject matter described here can improve the operation of a drug delivery device comprising the above described mechanism.

Certain aspects can be implemented with an operation member, with a mechanism and with a drug delivery device.

According to one aspect, the invention relates to an operation member comprising a central opening with a periphery and at least one protruding element arranged on the periphery and extending into the opening, which is surrounded by a protruding rim arranged on the periphery. The protruding rim is interrupted along the periphery by at least one gap. If more than one gap is provided, the gaps are arranged such that any rotation that keeps the opening in place and maps each of the gaps on one of the gaps comprises an integer multiple of 360°. This means that the pattern of the gaps does not comprise a symmetry that would allow a rotation different from an integer multiple of 360° around a central axis encircled by the periphery of the opening to map the complete pattern of gaps onto itself.

In an embodiment of the operation member, the at least one protruding element is arranged opposite the at least one gap.

In a further embodiment of the operation member, at least one further protruding element and at least one further gap are provided, and each of the protruding elements is arranged opposite one of the gaps.

In a further embodiment of the operation member, the opening is essentially circular, and the gap is confined by radii of the opening, which form an angle of less than 30°. The protruding rim may especially comprise at least three gaps, each of them being confined by radii forming an angle of less than 30°.

In a further embodiment of the operation member, the protruding rim comprises at least three gaps, the distance between any pair of these gaps being different from the distance between any further pair of these gaps unless the pair and the further pair are the same.

In a further embodiment of the operation member, the protruding rim comprises between four, five or six gaps.

In a further embodiment of the operation member, the opening is essentially circular, and the protruding rim comprises four gaps arranged on radii of the opening, so that different pairs of consecutive ones of these radii form an angle between 30° and 60°, an angle between 50° and 80°, an angle between 80° and 130° and an angle between 120° and 160°, the angles being different from one another.

In a further embodiment of the operation member, the protruding element and the protruding rim are arranged on different levels with respect to the periphery of the opening.

In a further embodiment of the operation member, at least one further protruding element is provided, and the protruding elements are arranged on the same level with respect to the periphery of the opening.

A further embodiment of the operation member comprises at least one grip provided for a dialling operation to be performed by a user. The operation member may in particular be a dial grip, which is gripped by a user to operate a mechanism, especially by rotating the dial grip, for example. The operation member may especially be used during a dose setting operation.

In a further embodiment of the operation member, the protruding rim is interrupted along the periphery by gaps, the gaps are arranged such that a rotation of the operation member that maps each of the gaps on one of the gaps comprises an integer multiple of 360°, and the at least one protruding element is arranged opposite to one of the gaps.

In a further aspect, the invention relates to a mechanism for a drug delivery device comprising such an operation member. A drive member of the mechanism is provided with an annular recess, and the protruding element of the operation member engages the annular recess.

During assembly, the end of the drive sleeve is allowed to enter the dose dial grip farther, so that the protruding parts reach a position beyond the annular recess of the drive sleeve, in order to facilitate assembly. If the drive sleeve reaches this position with respect to the dose dial grip during an operation of the mechanism, which may occur because of a misuse, the mechanism does not work properly or may even be damaged.

In an embodiment of the mechanism, at least two gaps are provided in the protruding rim of the operation member, and abutments are arranged on the drive member in positions corresponding to the gaps. Preferably, the abutments are dimensioned such that they may glide through the gaps when the operation member and the drive member are moved relatively to each other in a longitudinal direction. The pattern of the gaps and the corresponding abutments prevents the protruding parts from reaching a position beyond the annular recess of the drive sleeve except for one rotative position.

In a further embodiment of the mechanism, the protruding elements and the protruding rim of the operation member are arranged on different levels with respect to the periphery of the opening, and the angular recess and the abutments of the drive member are arranged on different levels, so that the protruding elements engage the angular recess with the protruding rim abutting on the abutments.

In a further embodiment of the mechanism, the gaps enable the abutments to enter the protruding rim, so that the protruding elements abut on the abutments beyond the angular recess.

A further embodiment of the mechanism comprises a piston rod, and the drive member is provided to advance the piston rod.

In a further aspect, the invention relates to a drug delivery device comprising such a mechanism.

The drug delivery device may be an injection device. The drug delivery device may be a pen-type device, in particular a pen-type injector. The device may be a disposable or a re-usable device, which comprises a cartridge holder for a replaceable cartridge. The device may be configured to dispense variable, preferably user-settable, doses of the drug. Alternatively, the device may be a fixed-dose device, in particular a device configured to dispense doses of the drug which may not be varied by the user. The drug delivery device may be a manually, in particular a non-electrically, driven device.

In particular, the drug delivery device may be a device as described in WO 2004/078239 A1, the content of which is hereby incorporated by reference.

The longitudinal axis of the mechanism may be a symmetry axis. The longitudinal axis of the mechanism may extend from a distal end of the mechanism to a proximal end of the mechanism. The longitudinal axis may be a central axis that is encircled by the periphery of the opening of the operation member. The term "distal end" designates that end of the mechanism which is to be arranged closest to a dispensing end of the drug delivery device when the mechanism is assembled into the drug delivery device. The term "proximal end" designates that end of the mechanism which is to be arranged furthest away from the dispensing end of the device. The longitudinal axis of the mechanism may be parallel to a longitudinal axis of the drug delivery device. The longitudinal axis of the drug delivery device may extend from a distal end of the device to a proximal end of the device.

The term "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39), wherein the group-Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains p and E have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The following is a detailed description of examples and embodiments of the operation member in conjunction with the appended figures.

Figure 1:
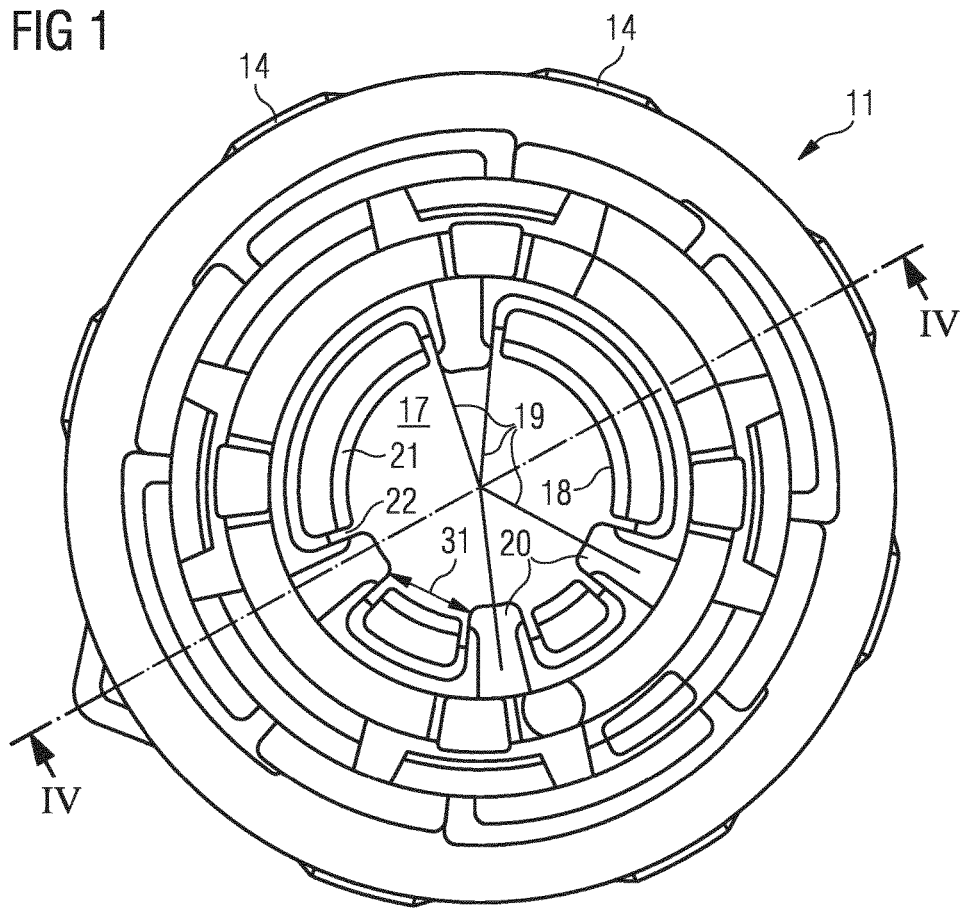
FIG. 1 is a cross section of an embodiment of the operation member.

FIG. 1 shows an embodiment of the operation member in a top view in the direction along a central axis. The operation member 11 is of a generally cylindrical shape and has a central opening 17. The outer circumference may be provided with grips 14 facilitating a rotation of the operation member 11 by a user. The operation member 11 may be used for dialling a dose of a drug that is to be administered, especially if the operation member 11 is applied as a component of a mechanism of a drug delivery device. The central opening 17 is generally cylindrical and has a periphery 18, which in the top view may be represented by a circle surrounding the opening 17.

FIG. 1 shows several radii 19 of the circle by way of examples. At least one protruding element 20 is provided at the periphery 18 of the opening 17. In the embodiment shown in FIG. 1, four protruding elements 20 are provided. The protruding elements 20 may especially be hooks or clamps engaging a further component of a mechanism. A protruding rim 21 limits the major part of the periphery 18 and comprises at least one gap 22 along the periphery 18. In the embodiment shown in FIG. 1, four gaps 22 are provided, and the protruding elements 20 are arranged opposite the gaps 22. Instead of the protruding elements 20, other elements may be arranged opposite the gaps 22 in order to prevent a further component of the mechanism, like a drive member, from being pushed farther than a predefined position. The gaps 22 may especially be confined by radii 19 of the opening 17 forming an angle of less than 30°, so that the gaps 22 are comparatively narrow.

Consecutive radii 19 passing through the centres of the gaps 22 preferably form different angles, so that the pattern of gaps 22 is irregular and unsymmetrical. This results in a complete lack of rotational symmetry of the pattern of gaps 22, which consequently cannot be mapped onto itself by a rotation around the central axis of the operation member 11, with the opening 17 kept in place, except for rotations by an integer multiple of 360°, of course. The different angles also imply different distances 31 between neighbouring gaps 22. Further details of the operation member 11 shown in FIG. 1 may be provided for individual embodiments, but they are not essential for an enabling disclosure of the invention and are not described.

Figure 2:
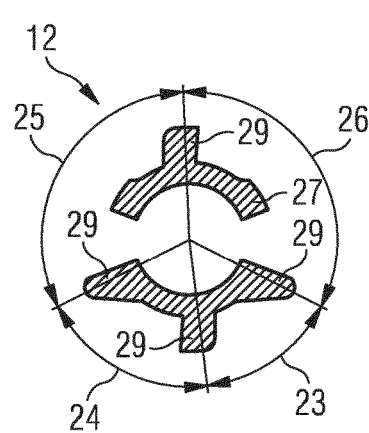
FIG. 2 is a detail of a drive member of a mechanism comprising the operation member.

FIG. 2 is a detail of a drive member 12 that is suitable to be combined with the operation member 11 in a mechanism of a drug delivery device. The drive member 12 may serve to advance a piston rod of a drive mechanism used to expel a drug from a container. The drive member 12 may especially be a drive sleeve. FIG. 2 shows a top view onto the proximal end 27 of the drive member 12, which may be a drive sleeve of generally cylindrical shape, for instance. At least one abutment 29 is provided on the proximal end 27 of the drive member 12. In the embodiment shown in FIG. 2, four abutments 29 are provided, with central lines of consecutive abutments 29 forming different angles 23, 24, 25, 26. These angles 23, 24, 25, 26 correspond to the angles formed by consecutive radii 19 passing through the centres of the gaps 22 in the protruding rim 21 of the operation member 11. The pattern of the gaps 22 is thus the same as the pattern of the abutments 29 of the drive member 12.

In embodiments a smallest first angle 23 may be from 30° to 60°, a second larger angle 24 from 50° to 80°, a third even larger angle 25 from 80° to 130°, and a largest fourth angle 26 from 120° to 160°. A typical example comprises a first angle 23 of approximately 55°, a second angle 24 of approximately 65°, a third angle 25 of approximately 115°, and a fourth angle 26 of approximately 125°, the four angles 23, 24, 25, 26 summing to 360°. Further examples of four different angles 23, 24, 25, 26 within the specified ranges are: 30°, 50°, 130° and 150°; 30°, 80°, 110° and 140°; 40°, 50°, 110° and 160°; 50°, 70°, 80° and 160°; 60°, 70°, 80° and 150°; or 60°, 80°, 100° and 120°.

Figure 3:
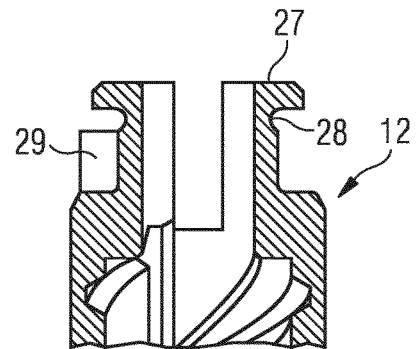
FIG. 3 is a cross section of the drive member of the mechanism.

FIG. 3 is a cross section of the drive member 12 at its proximal end 27. An annular recess 28, which is provided for an engagement of the protruding elements 20 of the operation member 11, is formed in the outer surface of the drive member 12 near its proximal end 27. The abutments 29 are arranged at a small distance below the annular recess 28.

Figure 4:
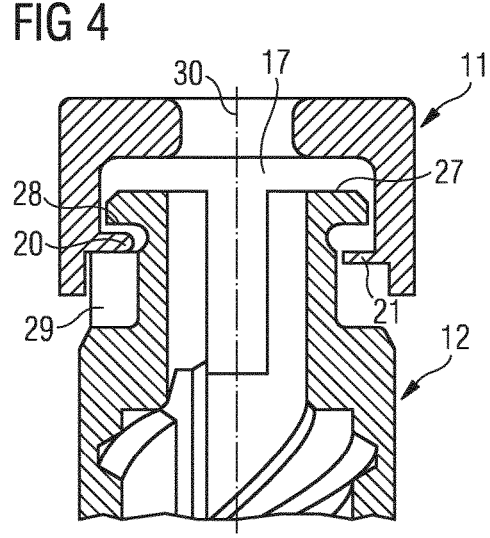
FIG. 4 is a cross section according to FIG. 3 of the operation member and the drive member assembled.

FIG. 4 is a cross section according to FIG. 3 of the operation member 11 and the drive member 12 assembled, so that the protruding elements 20 of the operation member 11 engage the annular recess 28 of the drive member 12. The position of the cross section of FIG. 4 is indicated in FIG. 1, which shows that one gap 22 is included in the cross section, where the relevant protruding element 20, shown on the left side in FIG. 4, abuts on the abutment 29 of the drive member 12, if the drive member 12 is pushed into the opening 17 of the operation member 11 as far as possible along the central axis 30, which is also the axis of rotation of these components. The relative axial movement of the operation member 11 and the drive member 12 is inhibited by the arrangement of the protruding elements 20 opposite the gaps 22. As has already been mentioned, the protruding elements 20 can be substituted with further elements arranged opposite the gaps 22, but an arrangement of the protruding elements 20 opposite the gaps 22 is preferred.

If each of the abutments 29 is located at the position of one of the gaps 22, the protruding rim 21 does not abut on any of the abutments 29, as shown on the right side of FIG. 4, and hence the drive member 12 can be shifted farther into the operation member 11 than would be possible if at least one of the abutments 29 were located opposite the protruding rim 21. In this special position, which is only once occupied during a complete rotation of the operation member 11 with respect to the drive member 12, owing to the lack of symmetry of the pattern of gaps 22, these components can therefore be approached until the protruding elements 20 reach a position that is a small distance beyond the position appropriate for regular use of the mechanism. This property is desired to facilitate the assembly of the mechanism. On the other hand, a damage of the mechanism due to a technical misuse is by far less probable than in conventional mechanisms, because the appropriate position of the drive member 12 with respect to the operation member 11 is secured by the protruding rim 21 and the abutments 29, except for only one rotative position during a complete relative rotation of the components around the central axis 30, as described above.

Figure 5:
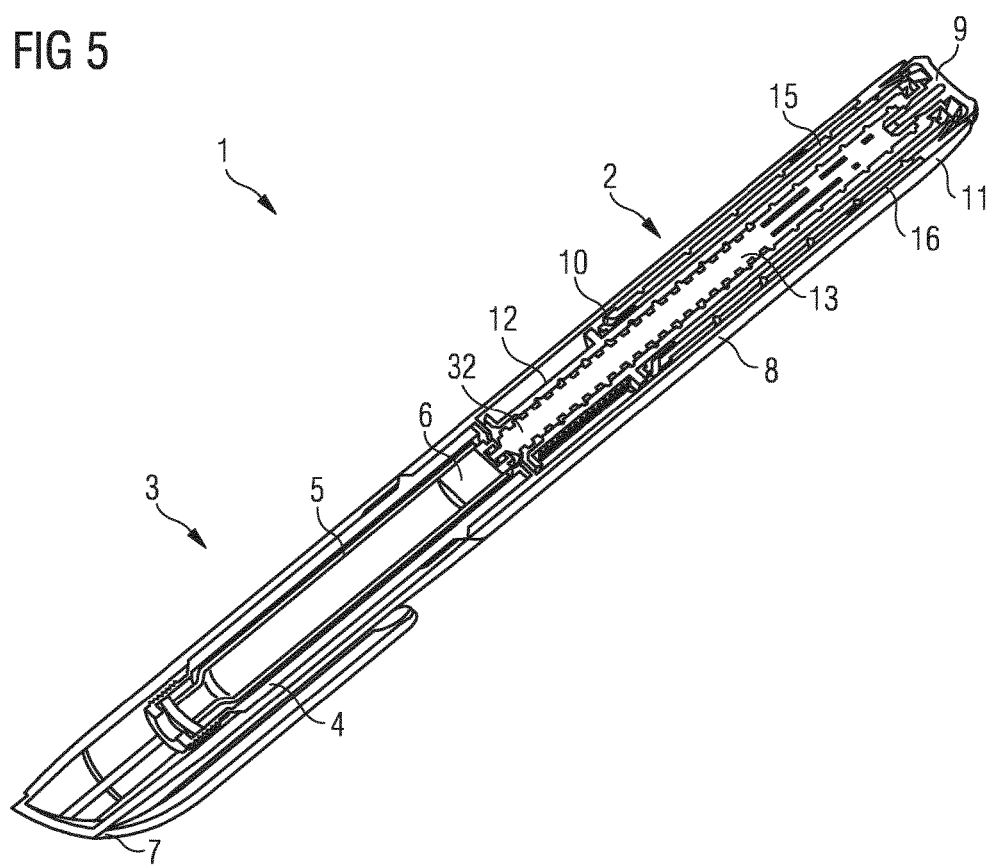
FIG. 5 shows a drug delivery device comprising the operation member and the mechanism.

FIG. 5 shows a cross-sectional view of a drug delivery device 1. The drug delivery device 1 comprises a drive mechanism 2 in a body 8, and optionally a cartridge sub-assembly 3 with a cartridge holder 4, which is configured to accommodate a cartridge 5 containing the drug to be dispensed. A piston 6 is retained in a proximal end of the cartridge 5. A removable cap 7 is releasably retained over a distal end of the cartridge sub-assembly 3 and can be replaced with an injection needle unit. The mechanism 2 comprises a button 9, a clutch 10, a dial grip 11, a drive member 12, a piston rod 13, a dose dial member 15 and an insert 16, which is secured against rotational or longitudinal movement relative to the body 8 and may especially be part of the body 8. The cartridge sub-assembly 3 is secured to the body 8. The body 8 may be a housing of the drug delivery device 1. The insert 16 is provided at the distal end with a threaded circular opening, which is engaged with the dial member 15. The piston rod 13 is threadedly engaged with the body 8 in a threaded circular opening 32 of the body 8. The dial grip 11 is rotationally and axially locked to the dial member 15.

To dial a dose, a user rotates the dial grip 11, and the dial member 15, the drive member 12 and the clutch 10 rotate together with the dial grip 11. The dial member 15 and the drive member 12 are moved in the proximal direction relative to the piston rod 13. When a desired dose has been dialled, the user may dispense the dose by depressing the button 9. This displaces the clutch 10 axially with respect to the dial member 15, thereby disengaging the clutch 10 from the dial member 15. By depressing the button 9, the drive member 12 is moved axially in the distal direction. This causes the piston rod 13 to rotate through the threaded circular opening 32 in the body 8, thereby advancing the piston 6 in the cartridge in the distal direction. After dose dispensing, the clutch 10 and the dial member 15 are reengaged.

REFERENCE NUMERALS 1 drug delivery device
2 drive mechanism
3 cartridge sub-assembly
4 cartridge holder
5 cartridge
6 piston
7 cap
8 body
9 button
10 clutch
11 operation member
12 drive member
13 piston rod
14 grip
15 dial member
16 insert
17 central opening
18 periphery
19 radius
20 protruding element
21 protruding rim
22 gap
23 angle
24 angle
25 angle
26 angle
27 proximal end of the drive member
28 annular recess
29 abutment
30 central axis
31 distance
32 threaded circular opening

The invention claimed is:

1. An operation member for a mechanism for a drug delivery device, the operation member comprising:
    a central opening with a periphery; and
    at least one protruding element arranged on the periphery and extending into the opening,
    wherein:
        the opening is surrounded by a protruding rim arranged on the periphery,
        the protruding rim is interrupted along the periphery by gaps,
        the at least one protruding element is arranged opposite a first one of the gaps, and
        the gaps are arranged such that any rotation of the operation member around the opening by less than 360 degrees, moving each of the gaps from an initial position to a final position, moves at least one of the gaps to a final position that is different from all initial positions of the gaps.

2. The operation member according to claim 1, wherein the at least one protruding element is a first protruding element, and wherein the operation member further comprises a second protruding element arranged opposite a second one of the gaps.

3. The operation member according to claim 1, wherein the opening is substantially circular and comprises a center, and the first one of the gaps is confined by two different rays from the center to the periphery of the opening, the rays enclosing an angle of less than 30 degrees.

4. The operation member according to claim 3, wherein the protruding rim comprises a second one and a third one of the gaps, each of the second one of the gaps and the third one of the gaps being confined by rays from the center to the periphery, the rays enclosing angles of less than 30 degrees.

5. The operation member according to claim 2, wherein the protruding rim comprises a third one of the gaps, a distance between the first one of the gaps and the second one of the gaps being different from a distance between the first one of the gaps and the third one of the gaps.

6. The operation member according to claim 1, wherein a number of the gaps of the protruding rim is four, five or six.

7. The operation member according to claim 1, wherein the opening is substantially circular and comprises a center, and four of the gaps of the protruding rim are arranged on different rays from the center to the periphery of the opening so that consecutive ones of the different rays enclose an angle between 30 degrees and 60 degrees, an angle between 50 degrees and 80 degrees, an angle between 80 degrees and 130 degrees and an angle between 120 degrees and 160 degrees, the angles being different from one another.

8. The operation member according to claim 1, wherein the at least one protruding element and the protruding rim are arranged on different levels with respect to the periphery of the opening.

9. The operation member according to claim 1, wherein the at least one protruding element is a first protruding element, wherein the operation member comprises a second protruding element, and the first protruding element and the second protruding element are arranged on the same level with respect to the periphery of the opening.

10. The operation member according to claim 1, further comprising at least one grip being provided for a dialling operation to be performed by a user.

11. A mechanism for a drug delivery device, the mechanism comprising:
    an operation member comprising:
        a central opening with a periphery; and
        at least one protruding element arranged on the periphery and extending into the opening,
    wherein:
        the opening is surrounded by a protruding rim arranged on the periphery,
        the protruding rim is interrupted along the periphery by gaps, and
        the gaps are arranged such that any rotation of the operation member around the opening by less than 360 degrees, moving each of the gaps from an initial position to a final position, moves at least one of the gaps to a final position that is different from all initial positions of the gap; and
    a drive member with an annular recess, the at least one protruding element of the operation member engaging the annular recess.

12. The mechanism according to claim 11, further comprising: abutments arranged on the drive member in positions corresponding to the gaps.

13. The mechanism according to claim 12, further comprising a plurality of protruding elements including the at least one protruding element, the plurality of protruding elements and the protruding rim of the operation member being arranged on different levels with respect to the periphery of the opening, and the annular recess and the abutments of the drive member being arranged on different levels, so that the plurality of protruding elements engage the annular recess with the protruding rim abutting on the abutments.

14. The mechanism according to claim 13, wherein the gaps enable the abutments to enter the protruding rim so that the protruding elements abut on the abutments beyond the annular recess.

15. The mechanism according to claim 11, further comprising:
    a piston rod, the drive member being provided to advance the piston rod.

16. A drug delivery device comprising:
    a mechanism for a drug delivery device, the mechanism comprising:
        an operation member comprising:
            a central opening with a periphery; and
            at least one protruding element arranged on the periphery and extending into the opening,
        wherein:
            the opening is surrounded by a protruding rim arranged on the periphery,
            the protruding rim is interrupted along the periphery by gaps, and
            the gaps are arranged such that any rotation of the operation member around the opening by less than 360 degrees, moving each of the gaps from an initial position to a final position, moves at least one of the gaps to a final position that is different from all initial positions of the gaps; and
        a drive member with an annular recess, the at least one protruding element of the operation member engaging the annular recess, wherein the drug delivery device is a pen-type injection device.

17. The drug delivery device according to claim 16, further comprising a cartridge holder for a replaceable cartridge.

* * * * *